US012806444B2

(12) United States Patent
Dempsey et al.

(10) Patent No.: US 12,806,444 B2
(45) Date of Patent: Nov. 24, 2026

(54) SYSTEMS, METHODS AND SOFTWARE FOR MAGNETIC RESONANCE IMAGE GUIDED RADIOTHERAPY

(71) Applicant: ViewRay Systems, Inc., Denver, CO (US)

(72) Inventors: James F. Dempsey, Pebble Beach, CA (US); Iwan Kawrykow, Sofia (BG)

(73) Assignee: ViewRay Systems, Inc., Denver, CO (US)

( * ) Notice: Subject to any disclaimer, the term of this patent is extended or adjusted under 35 U.S.C. 154(b) by 0 days.

(21) Appl. No.: 19/316,718

(22) Filed: Sep. 2, 2025

(65) Prior Publication Data

US 2025/0387646 A1 Dec. 25, 2025

Related U.S. Application Data

(63) Continuation of application No. 18/491,527, filed on Oct. 20, 2023, now Pat. No. 12,453,869.

(60) Provisional application No. 63/417,921, filed on Oct. 20, 2022.

(51) Int. Cl.
*A61N 5/10* (2006.01)
*G16H 20/40* (2018.01)

(52) U.S. Cl.
CPC ........... *A61N 5/1039* (2013.01); *G16H 20/40* (2018.01); *A61N 5/1037* (2013.01); *A61N 2005/1041* (2013.01); *A61N 2005/1055* (2013.01); *A61N 5/107* (2013.01); *A61N 2005/1072* (2013.01); *A61N 2005/1074* (2013.01)

(58) Field of Classification Search
CPC .......... A61N 5/1039; A61N 2005/1041; A61N 2005/1055; A61N 5/107; A61N 2005/1072; A61N 2005/1074
See application file for complete search history.

(56) References Cited

U.S. PATENT DOCUMENTS

2013/0218001 A1 8/2013 Uhlemann
2016/0213947 A1 7/2016 Han
2016/0228728 A1 8/2016 Dempsey

*Primary Examiner* — Colin T. Sakamoto
(74) *Attorney, Agent, or Firm* — Davis Graham & Stubbs LLP

(57) ABSTRACT

Systems, methods, and computer software are disclosed that can include receiving a treatment prescription for a patient, obtaining a diagnosis-driven magnetic resonance imaging guided radiotherapy treatment and planning workflow (MRgRT&P workflow) associated with the treatment prescription from a workflow library, the diagnosis-driven MRgRT&P workflow having a parameter list comprising parameters utilized for MRI-guided radiation therapy. With the diagnosis-driven MRgRT&P workflow, any of the following can be performed: imaging with the MRI-guided radiation therapy system utilizing radiation therapy imaging parameters in the parameter list, generating a radiation therapy treatment plan utilizing radiation therapy planning parameters in the parameter list, and/or controlling an MRI-guided radiation therapy system utilizing radiation therapy delivery parameters in the parameter list.

6 Claims, 3 Drawing Sheets

SYSTEMS, METHODS AND SOFTWARE FOR MAGNETIC RESONANCE IMAGE GUIDED RADIOTHERAPY

RELATED APPLICATION(S)

This application claims priority to and the benefit of U.S. Provisional Application No. 63/417,921, filed Oct. 20, 2022, titled "SYSTEMS, METHODS AND SOFTWARE FOR MAGNETIC RESONANCE IMAGE GUIDED RADIOTHERAPY," which is hereby incorporated by reference.

DESCRIPTION OF THE RELATED ART

Magnetic resonance imaging (MRI), or nuclear magnetic resonance imaging, is a noninvasive imaging technique that uses the interaction between radio frequency pulses, a strong magnetic field (modified with weak gradient fields applied across it to localize and encode or decode phases and frequencies) and body tissue to obtain projections, spectral signals, and images of planes or volumes from within a patient's body. Magnetic resonance imaging is particularly helpful in the imaging of soft tissues and may be used for the diagnosis of disease. Real-time or cine MRI may be used for the diagnosis of medical conditions requiring the imaging of moving structures within a patient. Real-time MRI may also be used in conjunction with interventional procedures, such as radiation therapy or image guided surgery.

SUMMARY

In one aspect, systems, methods, and computer software are disclosed that can include at least one programmable processor and a non-transitory machine-readable medium storing instructions which, when executed by the at least one programmable processor, cause the at least one programmable processor to perform operations comprising receiving a treatment prescription for a patient, obtaining a diagnosis-driven magnetic resonance imaging guided radiotherapy treatment and planning workflow (MRgRT&P workflow) associated with the treatment prescription from a workflow library, the diagnosis-driven MRgRT&P workflow having a parameter list comprising parameters utilized for MRI-guided radiation therapy. With the diagnosis-driven MRgRT&P workflow, any of the following can be performed: imaging with the MRI-guided radiation therapy system utilizing radiation therapy imaging parameters in the parameter list, generating a radiation therapy treatment plan utilizing radiation therapy planning parameters in the parameter list, and/or controlling an MRI-guided radiation therapy system utilizing radiation therapy delivery parameters in the parameter list.

In some variations, the treatment prescription can include disease type, treatment site, stage, total dose, number of fractions, dose per structure per fraction, min/max/mean dose constraints and/or dose volume constraints for targets and organs.

In some variations, the obtaining of the diagnosis-driven MRgRT&P workflow can include comparing the treatment prescription to stored treatment prescriptions associated with stored diagnosis-driven MRgRT&P workflows and returning a stored diagnosis-driven MRgRT&P workflow with a stored treatment prescription that matches the treatment prescription.

In some variations, the radiation therapy imaging parameters can include one or more of: volumetric imaging parameters, planar imaging parameters or tissue tracking parameters.

In some variations, the radiation therapy planning parameters can include one or more of: anatomy identification parameters, autocontouring parameters or relative electron density parameters.

In some variations, the radiation therapy delivery parameters can include one or more of: beam energy, MLC positions, or couch positions.

In some variations, the operations can include provision of a workflow editor configured to facilitate revision of the diagnosis-driven MRgRT&P workflow.

In some variations, the operations can include obtaining, from the workflow library, an additional diagnosis-driven magnetic resonance imaging guided radiotherapy treatment and planning workflow (MRgRT&P workflow) associated with the treatment prescription and presenting a user with multiple diagnosis-driven MRgRT&P workflows to choose from.

In an interrelated aspect, systems, methods, and computer software can include at least one programmable processor; and a non-transitory machine-readable medium storing instructions which, when executed by the at least one programmable processor, cause the at least one programmable processor to perform operations comprising: capturing initial parameters for a diagnosis-driven magnetic resonance imaging guided radiotherapy treatment and planning workflow (MRgRT&P workflow) associated with a treatment prescription, the capturing comprising recording initial parameters utilized during imaging with the MRI-guided radiation therapy system, utilized during generation of a radiation therapy treatment plan, and utilized during controlling of the MRI-guided radiation therapy system; generating the diagnosis-driven MRgRT&P workflow based on the initial parameters; and storing, in a workflow library, the diagnosis-driven MRgRT&P workflow, associated with the treatment prescription.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1:
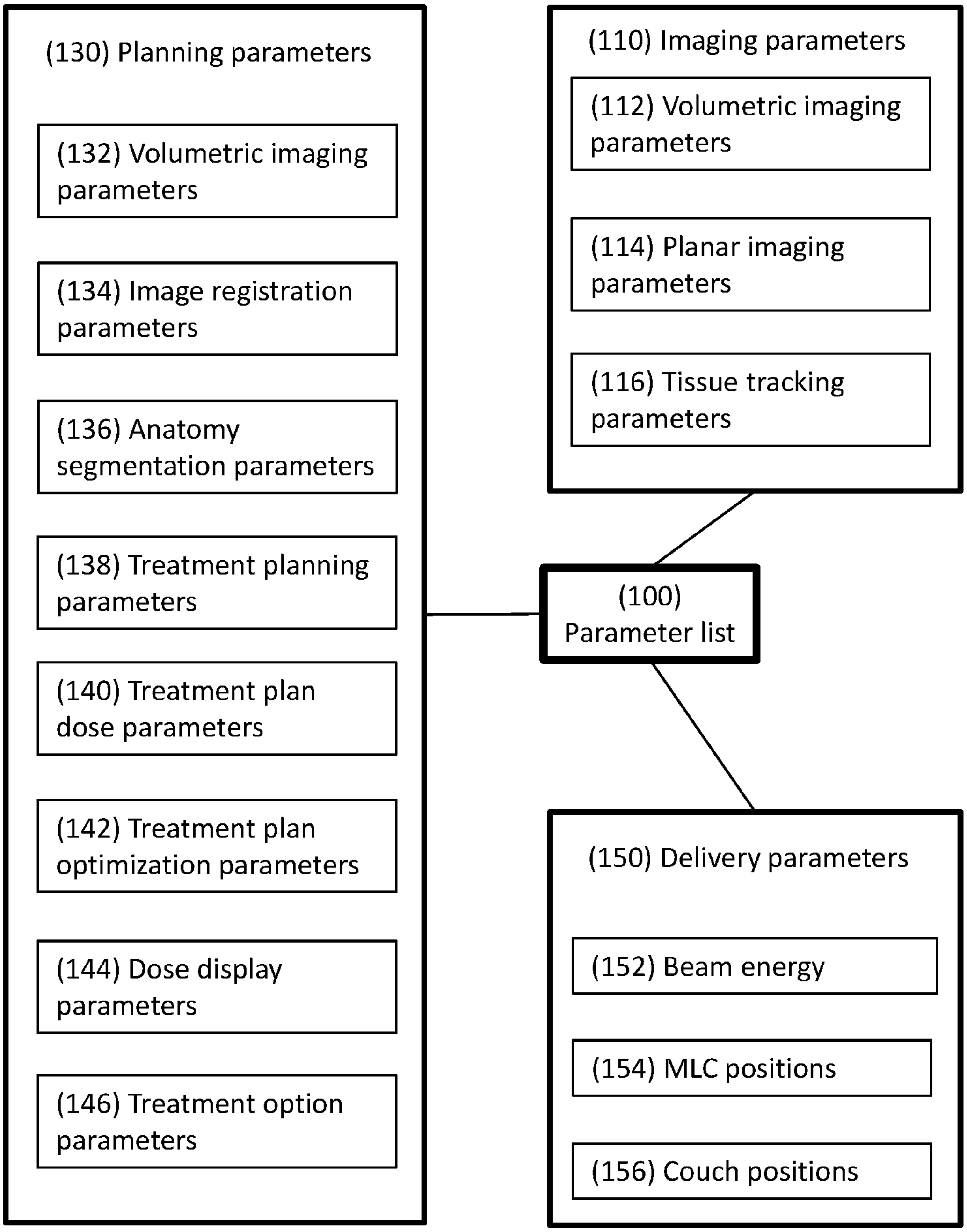
FIG. 1 is a diagram illustrating an exemplary listing of parameters that may be utilized with Magnetic Resonance Image Guided Radiation Therapy (MRgRT) imaging, planning or delivery in accordance with certain aspects of the present disclosure.

FIG. 1 is a diagram illustrating an exemplary listing of parameters that may be utilized with Magnetic Resonance Guided Radiation Therapy (MRgRT) imaging, planning and/or delivery in accordance with certain aspects of the present disclosure. MRgRT is an extraordinarily complex and precise process that can involve dozens (or even hundreds) of decisions during the course of planning and execution of a imaging/planning/treatment workflow. Planning treatment for patient can include not only determining a radiation treatment plan but also determining machine parameters (e.g., for the MRI and radiation source) utilized during treatment. The present disclosure generally divides such parameters (e.g., in the form of a parameter list 100) into three categories: imaging parameters 110, planning parameters 130, and delivery parameters 150. However, particular parameters can be utilized in more than one category. For example, some imaging parameters can be determined as part of imaging that is performed during the planning process and may also be used during imaging in the delivery process. Accordingly, in various embodiments, parameter list 100 can include any combination of the parameters described herein. However, the parameters disclosed herein are not intended to be an exhaustive list and other parameters utilized in planning, imaging and delivery may be included and should be considered within the scope of the present disclosure.

Radiation therapy imaging parameters 110 can include volumetric imaging parameters 112 (shown separately in FIG. 1, but similar to or the same as volumetric imaging parameters 132 used in planning). Other parameters can include planar imaging parameters 114 for cine imaging, for example, which cine is enabled for treatment, cine labels, cine notes, number of planes, orientation of planes (axial, sagittal, coronal, oblique), contrast, frame rate, slice thickness, in-plane resolution, cine origins, cine fields of view, etc. Further parameters can include tissue tracking parameters 116, for example, structures to track for each plane, method of tracking boundary creation for each tracked structure including isodose level threshold (> or <a dose level), boundary structure, or structure margin expansion in each specified direction (+x, −x, +y, −y, +z, −z). Gating parameters for each plane can include which soft tissue tracking algorithm (e.g., standard, large deforming, small mobile, etc.), percentage area violation allowed, confidence value in percentage, display setting for patient (e.g., hidden, contours only, image and contours), k-space blending on/off, noise filtering on/off with noise parameter, motion correction on/off, tracking off count in frames (e.g. 0-5), tracking on count in frames (e.g. 0-5), etc.

Radiation therapy planning parameters 130 can include one or more of: volumetric imaging parameters 132, image registration parameters 134, anatomy segmentation parameters 136, treatment planning parameters 138, treatment plan dose parameters 140, treatment plan optimization parameters 142, dose display parameters 144, treatment option parameters 146, etc.

Volumetric imaging parameters 132 for initial treatment planning and daily setup including can include, for example, the following parameters. Planned patient orientation can specify, for example, headfirst or feet first and prone or supine. Parameters for couch positions can be utilized to set the imaging volume. Parameters for anatomical site(s) such as known treatment locations (e.g., tumors) and/or organs at risk can be utilized for volume constraints or defaults (e.g., approximate sizes of tumors, lungs, heart, etc.). The number of scans and scan contrast (pulse sequence) for each scan can be set, as well as which scans are needed at treatment. Parameters relating to a skin mask algorithm can be used (e.g., to detect and define a skin surface outside of which volumetric imaging need not be performed), or parameters relating to thresholds for determination of the skin surface (e.g., a given intensity value or image gradient, a noise floor, etc.). In some embodiments, imaging parameters determined for pre-treatment imaging may also be used during treatment (e.g., for real-time MRgRT).

Some embodiments can include volumetric imaging parameters that may be set for each scan. For example, a scan label, scan notes, and scan position can be set. A field of view (FOV) can be set. The system can further accept or reject such settings based on a skin mask. For example, the FOV can be accepted if the skin mask is inside by more than 1 cm and not more than 2 cm and is expanded or contracted if not, so that a 1 cm margin is added if it is less and a 2 cm margin is set if larger. Configurations for parallel imaging can be set, e.g., parallel imaging along 0, 1, or 2 axes. Scan resolution can be set, for example having a higher resolution for critical features or ones having small dimensions and lower resolution in less-critical areas. Other parameters can include planned breath holding, such as for acquiring images at an inhale, exhale, or none, if breath holding is not used.

Image registration parameters 134 can include parameters for secondary image sets defined for deformable image registration to assist in planning, definition of an optional X-Ray CT scan to produce a relative electron density (RED) map, or a previously-delivered dose defined for deformable image registration, etc.

Anatomy segmentation parameters 136 can include definitions of targets and OARs for treatment planning, Boolean operators and rules for generating contours, autocontouring templates, definitions for synthetic CT generation, RED density overrides, color of each target or OAR, displaying segmentations as lines, with line thickness, and/or color wash on/off with percent opacity, etc.

Treatment planning parameters 138 can include the number of isocenters, isocenters locations, couch location relative to planning isocenters, number of beams at each isocenter, angles of each beam, type of each beam (e.g., conformal or intensity modulated radiation therapy (IMRT)), beam aperture creation rules for each conformal bean (e.g., structure and margin in each beam direction), etc.

Treatment plan dose parameters 140 can include bixel size (e.g., 4 mm×4 mm or 3 mm or 2 mm), dose grid resolution, IMRT efficiency (e.g., 0.2 to 20), bixel histories/$cm^2$ for Monte Carlo dose computation (e.g., 15,000), total segment histories for Monte Carlo dose computation (e.g., 4,800, 000), options to use magnetic field in bixel dose computation or use magnetic field in segment dose computation, etc.

Treatment plan optimization parameters 142 can include IMRT leaf sequencer type (e.g., fixed segments, accuracy goal, or fixed discretization), maximum leaf sequencer discretization (e.g., 1 to 16), leaf sequencer accuracy goal (e.g., 0.1 to 0.01), number of maximum segments, optimization objective function type (simple or advanced), etc. For targets and OARs in the advanced objective function, other parameters can include objective importance, objective power, whether increasing or decreasing, etc. For targets and OARs in the simple objective function, other parameters can include objective upper importance, objective lower importance, objective upper power, objective lower power, threshold dose, etc. For each target or OAR, other parameters can also include constraints such as min dose greater than or equal to, max dose less than or equal to, average dose greater than or equal to, average dose less than or equal to, etc. Parameters for dose volume histogram constraints for the advanced objective function for each target or OAR can include volume in percent or cc, greater than or equal to or less than or equal to, dose, etc.

Dose display parameters 144 can include the number of isodose lines, dose level of each isodose line, isodose line display in Gy or percent, color of each isodose line, thickness of isodose lines, opacity of isodose lines, dose color wash on or off, colormap of color wash, opacity of color wash, color wash display in Gy or percent, min color wash value, max color wash value, etc.

Treatment option parameters 146 can include adaptive or nonadaptive, populating the fraction delivery calendar with approved treatment plans, setting subsequent adaptive fractions to be the new online adapted plan or the original plan, etc.

In some embodiments, radiation therapy planning parameters that can be utilized for generating relative electron density (RED) settings or maps can also include anatomy identification parameters (e.g., coordinates or labelling of a structure or composition within the patient), autocontouring parameters (e.g., similar to anatomy segmentation parameters 116), relative electron density parameters (e.g., RED values assigned to identified anatomy), etc.

Radiation therapy delivery parameters 150 can include one or more of: beam energy 152, MLC positions 154 or couch positions 156. Such radiation therapy delivery parameters can thereby provide physical settings for the radiation delivery device (e.g., power sources engaged, MLC leaves at particular locations, treatment couch positioned at a particular height/orientation, etc.).

The present disclosure contemplates automating certain aspects of radiotherapy planning, imaging, and/or treatment. This can be done by utilizing parameters that were previously determined in the process of imaging, planning, and/or treatment of a patient having a particular diagnosis, per a particular treatment prescription. The parameters associated with the treatment prescription can constitute what is referred to herein as a diagnosis-driven MRgRT&P workflow (note that when the present disclosure uses this term, it contemplates that imaging parameters can be included in the workflow, as discussed herein, even though the acronym does not specifically include an "I").

Figure 2:
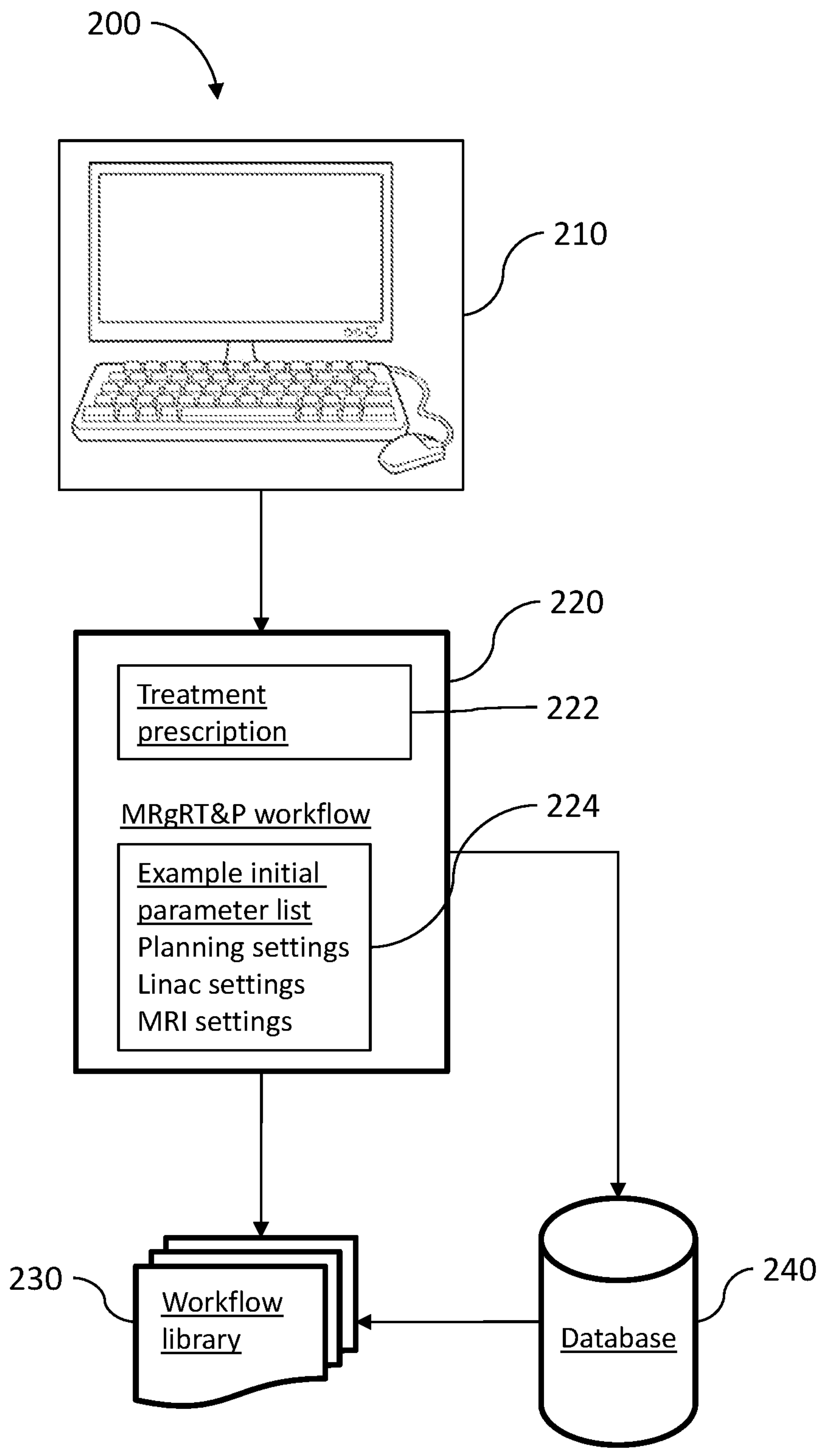
FIG. 2 is a diagram illustrating creation and storage of diagnosis-driven Magnetic Resonance Guided Radiotherapy Treatment and Planning (MRgRT&P) workflows in accordance with certain aspects of the present disclosure.

FIG. 2 is a simplified diagram illustrating the creation of a diagnosis-driven Magnetic Resonance-Guided Radiotherapy Treatment and Planning (MRgRT&P) workflow in accordance with certain aspects of the present disclosure. In some embodiments, the diagnosis-driven MRgRT&P workflow can be created through manual data entry of parameters such as those described above. In other embodiments, the diagnosis-driven MRgRT&P workflow may be created partially or fully through the capture of parameters utilized during an actual session of imaging, planning and/or treatment (for example, as performed by an expert or experienced clinician).

In the exemplary process 200 of FIG. 2, initial parameters of a diagnosis-driven MRgRT&P workflow associated with a treatment prescription can be captured at 210. Capturing can include recording initial parameters utilized during imaging with the MRI-guided radiation therapy system (e.g., any of imaging parameters 110), utilized during generation of a radiation therapy treatment plan (e.g., any of planning parameters 130), and/or utilized during the controlling of an MRI-guided radiation therapy system (e.g., any of delivery parameters 150). In one embodiment, the capturing can be performed by the system automatically capturing data entry fields, keystrokes or other manual computer input, etc.

At 220, a diagnosis-driven MRgRT&P workflow can be generated based on the captured parameters by associating a collection of initial parameters 224 with a diagnosis-driven MRgRT&P workflow. Any sub-combination of the captured initial parameters can used, for example, only certain parameters related to planning, imaging, delivery, planning and imaging, planning and delivery, or planning, imaging, and delivery may be included. In preferred embodiments, a diagnosis-driven MRgRT&P workflow includes parameters relating to the imaging, the planning and the treatment, but the present disclosure contemplates diagnosis-driven MRgRT&P workflows potentially including parameters relating only to a subset of those MRgRT operations.

The present disclosure also contemplates the system and software providing a workflow editor configured to facilitate revision of a diagnosis-driven MRgRT&P workflow. This can include utilizing a graphical user interface (GUI) to, for example, change numerical parameter values, modify anatomical contours, update labels, revise treatment objectives and constraints, modify imaging or radiation therapy machine settings, etc.

The diagnosis-driven MRgRT&P workflow can be associated with a treatment prescription 222. As used herein, the term "treatment prescription" broadly describes patent diagnosis and/or particular treatment parameters for a patient. For example, a treatment prescription can include any of: disease type (e.g., malignant or benign), treatment site, stage (T, N, M), grade, the primary reference target, intent (curative, palliative, other), total dose, number of fractions, dose per fraction, dose-volume constraints for targets including specifications of target prescription dose-volume coverage (e.g., the prescription dose (Drx) covers 95% or more of the target volume), target hot spot dose-volume allowance (e.g., less than 1 percent of the target volume is covered by greater than 107% of Drx), target cold spots dose-volume allowance (e.g., more than 99% of the target volume is covered by 95% of Drx), as well as dose-volume constraints for healthy organs-at-risk involved in the treatment of the given diagnosis (e.g., dose volume constraints for bladder, rectum, and femurs in the treatment of prostate cancer), minimum dose constraints for targets, mean dose constraints for targets and healthy organs-at-risk, maximum dose constraints for targets and healthy organs-at-risk, etc. Also, as used herein, “dose” can be physical dose in Gy or biologically effective dose (BED).

In some embodiments, there can be different (i.e., multiple) diagnosis-driven MRgRT&P workflows for a particular diagnosis. For example, when treating prostate cancer, a diagnosis-driven MRgRT&P workflow can provide parameters for treatment in a single fraction of 24 Gy, while other diagnosis-driven MRgRT&P workflows may treat in, e.g., 5 fractions of 8 Gy or 39 fractions of 2 Gy, as each of these treatment plans will deliver a similar biological effective dose.

It is also contemplated that there can be different (i.e., multiple) diagnosis driven MRgRT&P workflows for a given treatment prescription. For example, different workflows for the same prescription may include different optimization parameters for planning (e.g., treatment plan optimization parameters 142, etc.). The different optimization settings can then provide different plans that may result in somewhat different dose to target, organ sparing, etc., and a user may utilize more than one of the workflows in order to compare similar plans and choose a desired one.

At 230, the diagnosis-driven MRgRT&P workflow can be stored in a workflow library, associated with the treatment prescription. A workflow library can be any data store and can include other diagnosis-driven MRgRT&P workflows that may be created for other treatment prescriptions. In other embodiments, diagnosis-driven MRgRT&P workflows can be stored in a database 240 (e.g., a local server or other computer memory) that can be accessed by workflow library 230 to bring in any number of diagnosis-driven MRgRT&P workflows 220.

Figure 3:
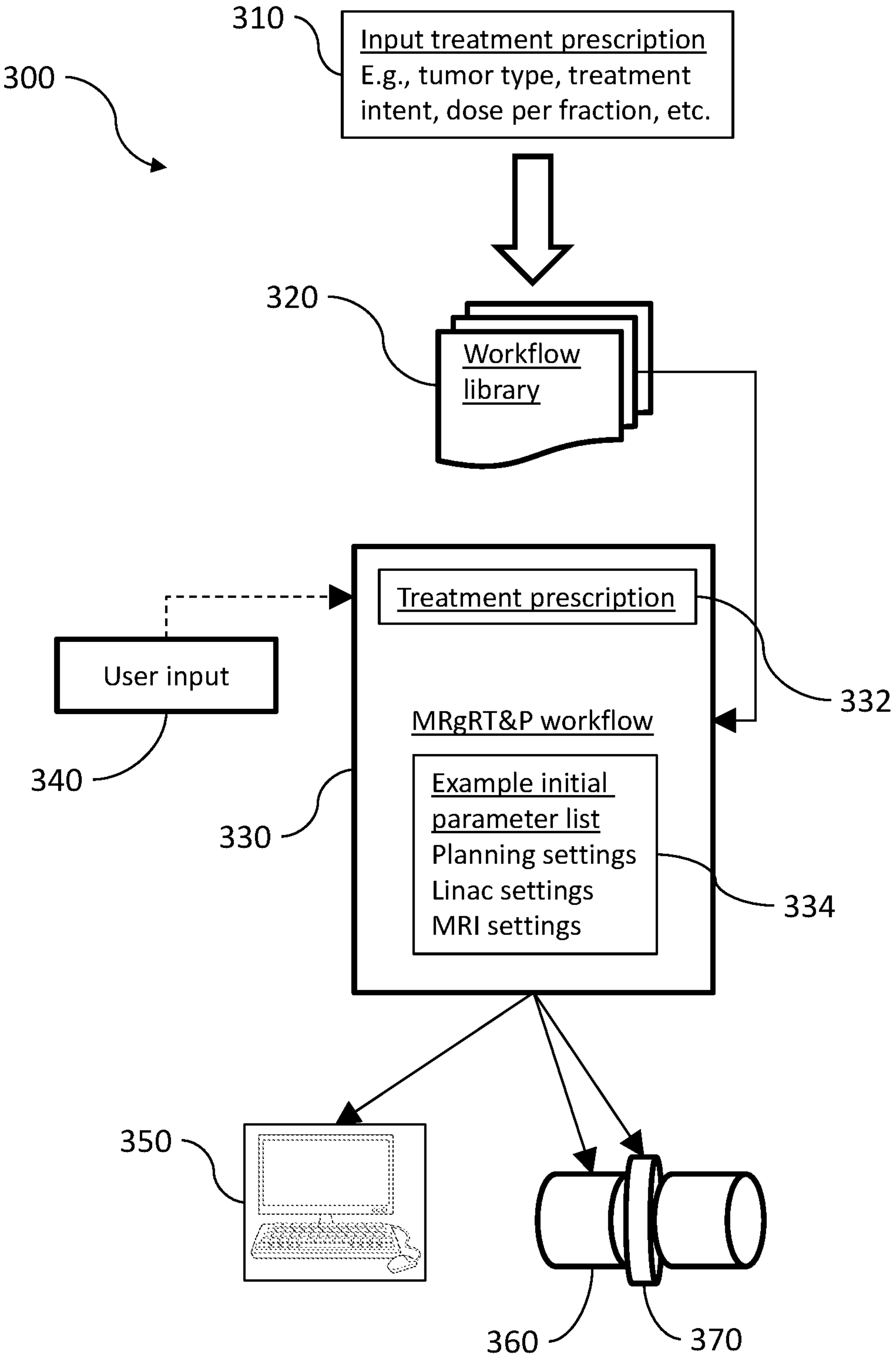
FIG. 3 is a diagram illustrating use of a diagnosis-driven MRgRT&P workflow in accordance with certain aspects of the present disclosure.

FIG. 3 is a diagram illustrating an exemplary use of a diagnosis-driven MRgRT&P workflow in accordance with certain aspects of the present disclosure. Process 300 can include, at 310, receiving a treatment prescription for a patient, for example, by the system interpreting entered clinician text or fields, selection of preestablished treatment prescriptions (e.g., from a list), etc. For example, a treatment prescription can include disease type, treatment site, stage, total dose, number of fractions, dose per structure per fraction, min/max/mean dose constraints and/or dose volume constraints for targets and organs, etc.

At 320, a diagnosis-driven MRgRT&P workflow 330 associated with the treatment prescription 332 can be obtained from a workflow library 320. The diagnosis-driven MRgRT&P workflow 330 can include parameter list 334 having parameters utilized for MRI-guided radiation therapy. For example, given the treatment prescription input at 310, the appropriate diagnosis-driven MRgRT&P workflow can be found in workflow library 320 by, for example, comparing the treatment prescription to stored treatment prescriptions associated with stored diagnosis-driven MRgRT&P workflows. The system can then return a stored diagnosis-driven MRgRT&P workflow with a stored treatment prescription that matches the treatment prescription. Parameter list 334 can include the parameters previously created and stored during the creation process (e.g., as described with reference to FIG. 2).

In some cases, the system may return multiple different diagnosis-driven MRgRT&P workflows to a user for selection. For example, workflows for a particular treatment prescription may include different optimization parameters for planning and a user can be presented with the multiple workflows and utilize/select the one considered most desirable. Thus, the system can be configured to obtain, from the workflow library, an additional diagnosis-driven magnetic resonance imaging guided radiotherapy treatment and planning workflow (MRgRT&P workflow) associated with the treatment prescription and present a user with multiple diagnosis-driven MRgRT&P workflows to choose from.

The diagnosis-driven MRgRT&P workflow 330 can be utilized for planning, imaging, treatment, etc., but some embodiments allow, at 340, for editing of the diagnosis-driven MRgRT&P workflow before use. For example, various parameters can be modified by a physician or technician based on the particular needs of the patient or a imaging/planning/delivery system configuration. However, such manual requirements are dramatically reduced due to the present disclosure’s automatic recall and application of previously determined parameters in the diagnosis-driven MRgRT&P workflow.

With the recalled diagnosis-driven MRgRT&P workflow 330, the system can then perform any combination of imaging with the MRI-guided radiation therapy system 360 utilizing radiation therapy imaging parameters in parameter list 334, generating a radiation therapy treatment plan utilizing radiation therapy planning parameters in parameter list 334 (at 350 in FIG. 3), and controlling an MRI-guided radiation therapy system utilizing the radiation therapy delivery parameters in parameter list 334 (at 370, represented in FIG. 3 by the exemplary gantry-mounted radiation therapy system within a split MRI).

While the embodiment described above can be utilized for imaging, planning and treatment, other embodiments can include those where the diagnosis-driven MRgRT&P workflow 330 is utilized in sub-combinations with any one or any two of those phases. In one embodiment, the system can generate a radiation therapy treatment plan utilizing the radiation therapy planning parameters in parameter list 334 and control the MRI-guided radiation therapy system utilizing the radiation therapy delivery parameters in the parameter list. In another embodiment, the system can image with the MRI-guided radiation therapy system utilizing the radiation therapy imaging parameters in parameter list 334 and generate the radiation treatment plan utilizing the radiation therapy planning parameters in parameter list 334. In yet another embodiment, the system can image with the MRI-guided radiation therapy system utilizing the radiation therapy imaging parameters in parameter list 334 and control the MRI-guided radiation therapy system utilizing the radiation therapy delivery parameters in parameter list 334. In other embodiments, the system can be configured for any one of imaging with the MRI-guided radiation therapy system utilizing radiation therapy imaging parameters in parameter list 334, generating a radiation therapy treatment plan utilizing radiation therapy planning parameters in parameter list 334, or controlling an MRI-guided radiation therapy system utilizing radiation therapy delivery parameters in parameter list 334.

In some implementations, the processes described herein can further include requesting user confirmations relating to the generating, imaging and/or controlling based on the parameter list 334. For example, the system can require confirmation of parameters in the diagnosis-driven MRgRT&P workflow at various steps through the process to make sure the user wants to proceed in the manner specified.

In the following, further features, characteristics, and exemplary technical solutions of the present disclosure will be described in terms of items that may be optionally claimed in any combination:

Item 1: A system comprising at least one programmable processor and a non-transitory machine-readable medium storing instructions which, when executed by the at least one programmable processor, cause the at least one programmable processor to perform operations comprising: receiving a treatment prescription for a patient; obtaining, from a workflow library, a diagnosis-driven magnetic resonance imaging guided radiotherapy treatment and planning workflow (MRgRT&P workflow) associated with the treatment prescription, the diagnosis-driven MRgRT&P workflow having a parameter list comprising parameters utilized for MRI-guided radiation therapy; imaging with the MRI-guided radiation therapy system utilizing radiation therapy imaging parameters in the parameter list; generating a radiation therapy treatment plan utilizing radiation therapy planning parameters in the parameter list; and/or controlling an MRI-guided radiation therapy system utilizing radiation therapy delivery parameters in the parameter list.

Item 2: the system of Item 1: wherein the treatment prescription includes disease type, treatment site, stage, total dose, number of fractions, dose per structure per fraction, min/max/mean dose constraints and/or dose volume constraints for targets and organs.

Item 3: the system as in of any one of the preceding Items, the obtaining of the diagnosis-driven MRgRT&P workflow comprising: comparing the treatment prescription to stored treatment prescriptions associated with stored diagnosis-driven MRgRT&P workflows; and returning a stored diagnosis-driven MRgRT&P workflow with a stored treatment prescription that matches the treatment prescription.

Item 4: the system as in of any one of the preceding Items, wherein the radiation therapy planning parameters include one or more of: anatomy identification parameters, autocontouring parameters or relative electron density parameters.

Item 5: the system as in of any one of the preceding Items, wherein the radiation therapy planning parameters include one or more of: volumetric imaging parameters, image registration parameters, anatomy segmentation parameters, treatment planning parameters, treatment plan dose computation parameters, treatment plan optimization parameters, dose display parameters or treatment option parameters.

Item 6: the system as in of any one of the preceding Items, wherein the radiation therapy imaging parameters include one or more of: volumetric imaging parameters, planar imaging parameters or tissue tracking parameters.

Item 7: the system as in of any one of the preceding Items, wherein the radiation therapy delivery parameters include one or more of: beam energy, MLC positions, or couch positions.

Item 8: the system as in of any one of the preceding Items, the operations further comprising requesting user confirmations relating to the generating, imaging and/or controlling based on the parameter list.

Item 9: the system as in of any one of the preceding Items, the operations further comprising provision of a workflow editor configured to facilitate revision of the diagnosis-driven MRgRT&P workflow.

Item 10: the system as in of any one of the preceding Items, the operations further comprising: obtaining, from the workflow library, an additional diagnosis-driven magnetic resonance imaging guided radiotherapy treatment and planning workflow (MRgRT&P workflow) associated with the treatment prescription; and presenting a user with multiple diagnosis-driven MRgRT&P workflows to choose from.

Item 11: A system comprising: at least one programmable processor; and a non-transitory machine-readable medium storing instructions which, when executed by the at least one programmable processor, cause the at least one programmable processor to perform operations comprising: capturing initial parameters for a diagnosis-driven magnetic resonance imaging guided radiotherapy treatment and planning workflow (MRgRT&P workflow) associated with a treatment prescription, the capturing comprising recording initial parameters utilized during imaging with the MRI-guided radiation therapy system, utilized during generation of a radiation therapy treatment plan, and utilized during controlling of the MRI-guided radiation therapy system; generating the diagnosis-driven MRgRT&P workflow based on the initial parameters; and storing, in a workflow library, the diagnosis-driven MRgRT&P workflow, associated with the treatment prescription.

Item 12: the system as in Item 11, the operations further comprising provision of a workflow editor configured to facilitate revision of the diagnosis-driven MRgRT&P workflow.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A system comprising:

at least one programmable processor; and a non-transitory machine-readable medium storing instructions which, when executed by the at least one programmable processor, cause the at least one programmable processor to perform operations comprising:

capturing initial parameters for a diagnosis-driven magnetic resonance imaging guided radiotherapy treatment and planning workflow (MRgRT&P workflow) associated with a treatment prescription, the capturing comprising recording initial parameters utilized during imaging with an MRI-guided radiation therapy system, utilized during generation of a radiation therapy treatment plan, and utilized during controlling of the MRI-guided radiation therapy system;

generating the diagnosis-driven MRgRT&P workflow based on the initial parameters; and storing, in a workflow library, the diagnosis-driven MRgRT&P workflow, associated with the treatment prescription.

2. The system of claim 1, the operations further comprising provision of a workflow editor configured to facilitate revision of the diagnosis-driven MRgRT&P workflow.

3. The system of claim 1, wherein the initial parameters utilized during generation of the radiation therapy treatment plan include one or more of: anatomy identification parameters, autocontouring parameters or relative electron density parameters.

4. The system of claim 1, wherein the initial parameters utilized during generation of the radiation therapy treatment plan include one or more of: volumetric imaging parameters, image registration parameters, anatomy segmentation parameters, treatment planning parameters, treatment plan dose computation parameters, treatment plan optimization parameters, dose display parameters or treatment option parameters.

5. The system of claim 1, wherein the initial parameters utilized during imaging with an MRI-guided radiation therapy system include one or more of: volumetric imaging parameters, planar imaging parameters or tissue tracking parameters.

6. The system of claim 1, wherein the initial parameters utilized during controlling of the MRI-guided radiation therapy system include one or more of: beam energy, MLC positions, or couch positions.

* * * * *